United States Patent
Fathallah et al.

(10) Patent No.: US 8,231,578 B2
(45) Date of Patent: Jul. 31, 2012

(54) SYSTEM AND METHOD FOR SEQUENCING CHANNELS IN A MULTI-CHANNEL INFUSION PUMP

(75) Inventors: Marwan A. Fathallah, Mundelein, IL (US); Geoffrey N. Holland, Wadsworth, IL (US); Martin A. McNeela, Encinitas, CA (US); Bernardino Rubalcaba, Jr., Escondido, CA (US); Katalin M. Schroeder, Kenosha, WI (US); Patrick B. Keely, Grayslake, IL (US); Mihaela Cozmi, Gilroy, CA (US); Glenn Davis, Grayslake, IL (US); Suzanne Willey, San Diego, CA (US); Raymond P. Silkaitis, Lake Forest, IL (US)

(73) Assignee: Hospira, Inc., Lake Forest, IL (US)

( * ) Notice: Subject to any disclaimer, the term of this patent is extended or adjusted under 35 U.S.C. 154(b) by 487 days.

(21) Appl. No.: 12/038,507

(22) Filed: Feb. 27, 2008

(65) Prior Publication Data
US 2008/0243055 A1    Oct. 2, 2008

Related U.S. Application Data

(60) Provisional application No. 60/892,085, filed on Feb. 28, 2007.

(51) Int. Cl.
*A61M 31/00*   (2006.01)
*A61M 1/00*    (2006.01)
(52) U.S. Cl. .............. 604/151; 604/131; 604/500
(58) Field of Classification Search ............. 604/131, 604/65, 67, 890.1–892.1, 500, 151–155
See application file for complete search history.

(56) References Cited

U.S. PATENT DOCUMENTS

| | | | |
|---|---|---|---|
| 4,270,532 A | 6/1981 | Franetzki et al. | |
| 4,553,958 A | 11/1985 | LeCocq | |
| 4,559,036 A * | 12/1985 | Wunsch | 604/81 |
| 4,696,671 A | 9/1987 | Epstein et al. | |
| 5,041,086 A | 8/1991 | Koenig et al. | |
| 5,366,346 A | 11/1994 | Danby | |
| 5,382,232 A | 1/1995 | Haque et al. | |
| 5,395,320 A | 3/1995 | Padda et al. | |
| 5,464,392 A | 11/1995 | Epstein et al. | |
| 5,522,798 A * | 6/1996 | Johnson et al. | 604/65 |
| 5,573,502 A | 11/1996 | LeCocq et al. | |
| 5,713,856 A * | 2/1998 | Eggers et al. | 604/65 |

(Continued)

FOREIGN PATENT DOCUMENTS
EP    0 319 272    6/1989
(Continued)

*Primary Examiner* — Theodore Stigell
*Assistant Examiner* — Leah Stohr
(74) *Attorney, Agent, or Firm* — Michael R. Crabb

(57) ABSTRACT

A system, method, and computer program for controlling at least one infusion pump wherein the system comprises a first channel for delivering a first fluid, a second channel for delivering a second fluid, a first input for receiving channel sequence data wherein the channel sequence data identifies the sequence for delivering the first fluid from the first channel and the second fluid from the second channel, a second input for receiving first delivery data for the first channel and the second delivery data for the second channel, and a processor for controlling delivery of the first fluid from the first channel and the second fluid from the second channel according to the channel sequence data, the first delivery data, and the second delivery data.

10 Claims, 16 Drawing Sheets

U.S. PATENT DOCUMENTS

| | | | |
|---|---|---|---|
| 5,745,378 A | 4/1998 | Barker et al. | |
| 5,772,635 A | 6/1998 | Dastur et al. | |
| 5,782,805 A | 7/1998 | Meinzer et al. | |
| 5,814,015 A * | 9/1998 | Gargano et al. | 604/67 |
| 5,904,668 A | 5/1999 | Hyman et al. | |
| 5,956,023 A | 9/1999 | Lyle et al. | |
| 6,773,412 B2 | 8/2004 | O'Mahony | |
| 6,852,104 B2 | 2/2005 | Blomquist | |
| 6,985,870 B2 | 1/2006 | Martucci et al. | |
| 7,029,456 B2 | 4/2006 | Ware et al. | |
| 7,103,419 B2 | 9/2006 | Engelson et al. | |
| 7,117,041 B2 | 10/2006 | Engelson et al. | |
| 2002/0007116 A1 * | 1/2002 | Zatezalo et al. | 600/432 |
| 2005/0022274 A1 | 1/2005 | Campbell et al. | |
| 2006/0106649 A1 | 5/2006 | Eggers et al. | |
| 2006/0140798 A1 | 6/2006 | Kutsuzawa | |
| 2006/0229557 A1 | 10/2006 | Fathallah et al. | |
| 2009/0177188 A1 * | 7/2009 | Steinkogler | 604/890.1 |

FOREIGN PATENT DOCUMENTS

| | | |
|---|---|---|
| JP | 1-308568 | 12/1989 |
| WO | 84/00894 | 3/1984 |

* cited by examiner

SYSTEM AND METHOD FOR SEQUENCING CHANNELS IN A MULTI-CHANNEL INFUSION PUMP

CROSS REFERENCE TO RELATED APPLICATIONS

This application claims priority based upon U.S. Provisional Application Ser. No. 60/892,085 filed Feb. 28, 2007 which is expressly incorporated herein by reference in its entirety.

TECHNICAL FIELD

The present invention generally relates to a system and method for controlling an infusion pump, and more particularly to a method and system for programming and operating a multi-channel infusion pump system to dispense fluid in a specific sequence.

BACKGROUND

Modern medical devices, including medical pumps, are increasingly being controlled by microprocessor based systems to deliver fluids, solutions, medications, and drugs to patients. A typical control for a medical pump includes a user interface enabling a medical practitioner to enter the dosage of fluid to be delivered, the rate of fluid delivery, the duration, and the volume of a fluid to be infused into a patient. Typically, drug delivery is programmed to occur as a continuous infusion or as a single bolus dose.

It is common for a plurality of fluids to be infused to a patient by using a multi-channel infusion pump or using a plurality of single channel infusion pumps where a different fluid is administered from each channel. Another method of infusing multiple fluids to a patient is the piggyback method.

The piggyback method allows an infusion pump to deliver fluid from a secondary container at a rate and volume similar to or different from that of a primary container. Typically, the fluid paths from the primary container and secondary container meet at a Y-joint intersection located above or upstream of the pump. Downstream of the Y-site, the IV tube set is then inserted into a single channel of an infusion pump. The secondary container must be suspended at a higher position on the IV pole so that the resulting higher head height creates a higher pressure in the IV tube. The microprocessor is programmed to stop an infusion and allow the user to switch the source of the infusion. With its superior pressure, the secondary container's flow interrupts the flow from the first container and allows a different fluid to be infused through the single channel on an interrupt basis. This method requires manual intervention, may require additional mechanical components such as a clamp or valve, and requires that multiple medications be delivered through a single channel. At the end of the secondary infusion, the secondary bag must generally be removed and infusion from the primary bag must be manually restarted.

Another method for infusing multiple fluids is disclosed in U.S. Pat. No. 4,696,671 and U.S. Pat. No. 5,464,392. In the infusion pump disclosed therein, a complex pump cassette with plural inlets and a single outlet is used to sequence and mix the flow of fluids from multiple sources through a single tube set. A plurality of valves must be included in the pump and operated by its processor according to a real time clock to control the flow of fluid through the cassette. This was a significant improvement over the manual manipulation of clamps, Y-sites, and valves that had been required, but moving the valves to the pump and automating them significantly added to the cost and complexity of the pump. Furthermore, the cassette could not be removed from the pump so long as any one of the plurality of inlet ports were being utilized to pump fluid from any of the sources. The single outlet of the cassette also fails to provide the flexibility to deliver the fluids through separate and distinct outlet or tubes to the patient, which may be desirable.

Another method for infusing multiple fluids is the use of a multi-channel infusion pump which delivers a separate fluid through each channel. In such infusion pumps, an individual therapy that is being delivered through a particular channel would have to be programmed and completely dispensed through that channel. After that individual therapy was dispensed, a new therapy on another channel could be programmed and dispensed. In this manner, multiple channels could not be programmed at a single time. Instead, each channel had to be programmed and started individually. As a result, the method was manual and required excessive user intervention. The present invention is provided to solve these and other problems.

SUMMARY

The present invention relates to a system for controlling at least one infusion pump. The system includes a first channel for delivering a first fluid and a second channel for delivering a second fluid. The first channel and the second channel may be located on a single infusion pump, or alternatively, the first channel may be located on a first infusion pump and the second channel may be located on a second infusion pump, wherein the first infusion pump and the second infusion pump are in communication with each other. The first infusion pump and second infusion pump may be detachably coupled to each other.

The system may further include a first tube set operably coupled with the first channel and a second tube set operably coupled with the second channel, wherein when the first fluid is being delivered from the first channel, the second tube set is capable of being removed from the second channel.

The system may also include a first input for receiving channel sequence data. The channel sequence data identifies the sequence for delivering the first fluid from the first channel and the second fluid from the second channel. In one example, the channel sequence data ensures that the first fluid will be delivered from the first channel and, after completion of the first fluid delivery, the second fluid will be delivered. In another example, the channel sequence data ensures that the first fluid will be delivered from the first channel and the second fluid will be concurrently delivered from the second channel.

Further, the system may include a second input for receiving first delivery data for the first channel, and second delivery data for the second channel. The delivery data may include fluid identification data, dosage data, rate data, fluid volume data, or delivery time data.

The system may also include a processor for controlling delivery of the first fluid from the first channel and the second fluid from the second channel, according to the channel sequence data, the first delivery data, and the second delivery data. The processor may also control the delivery of a keep vein open therapy after delivery of the first fluid and the second fluid.

In addition, the system may include a display that is capable of displaying the infusion data for a selected channel when fluid is being delivered from the selected channel, channel sequence data, first delivery data, or second delivery data.

In another aspect, the present invention relates to a computer program on a computer readable medium for controlling at least one infusion pump.

The computer program includes a code segment for receiving channel sequence data wherein the channel sequence data identifies a sequence for delivering fluid from at least two of a plurality of channels. The plurality of channels are located on a single infusion pump or alternatively, the plurality of channels are located on a plurality of infusion pumps. The plurality of infusion pumps are in communication with each other and may be detachably coupled to each other. Moreover, the plurality of channels may comprise a first channel and a second channel, and the channel sequence data identifies the sequence for delivering the fluid from the first channel and the second channel.

The computer program may also include a code segment for receiving delivery data for at least two of the plurality of channels. The channel sequence data may identify that the fluid from at least two of a plurality of channels will be delivered concurrently or sequentially. Further, the delivery data may include at least one of the variables selected from the group including fluid identification data, dosage data, rate data, fluid volume data, and delivery time data. The computer program may also include a code segment for controlling the delivery of the fluid from at least two of the plurality of channels according to the channel sequence data and the delivery data for at least two of the plurality of channels.

The computer program may also include a code segment for displaying the delivery data for each of the plurality of channels, and a code segment for displaying the sequence for delivering fluid from each of the plurality of channels.

In yet another aspect, the present invention includes a method for controlling an infusion pump. The method comprises the steps of inputting channel sequence data wherein the channel sequence data identifies the sequence for delivering a first fluid from a first channel and a second fluid from a second channel; inputting first delivery data for the first channel and second delivery data for the second channel; and, delivering the first fluid from the first channel and second fluid from the second channel according to the inputted channel sequence data, the first delivery data, and the second delivery data.

The first channel and the second channel may be located on a single infusion pump, or alternatively, the first channel may be located on a first infusion pump and the second channel may be located on a second infusion pump, wherein the first infusion pump and the second infusion pump are in communication with each other. The first infusion pump and second infusion pump may be detachably coupled to each other. The infusion pump may also include a first tube set operably coupled to the first channel and a second channel set operably coupled to the second channel. In one example, when the first fluid is being delivered from the first channel, the second tube set is capable of being removed from the second channel.

Further, the channel sequence data may enable the first fluid from the first channel and the second fluid from the second channel to be delivered sequentially or concurrently. A time offset may be programmed with respect to one or more deliveries to provide for delayed start, partially concurrent delivery, fully concurrent delivery, or delayed sequential delivery. In addition, the delivery data may include fluid identification data, dosage data, rate data, fluid volume data, or delivery time data.

The method may further include a step of displaying data selected from a group consisting of the infusion data for a selected channel when fluid is being delivered from the selected channel, the channel sequence data, first delivery data, and second delivery data. Moreover, the method may include a step of controlling a delivery of a keep vein open therapy after delivery of the first fluid and the second fluid.

DETAILED DESCRIPTION

Figure 1:
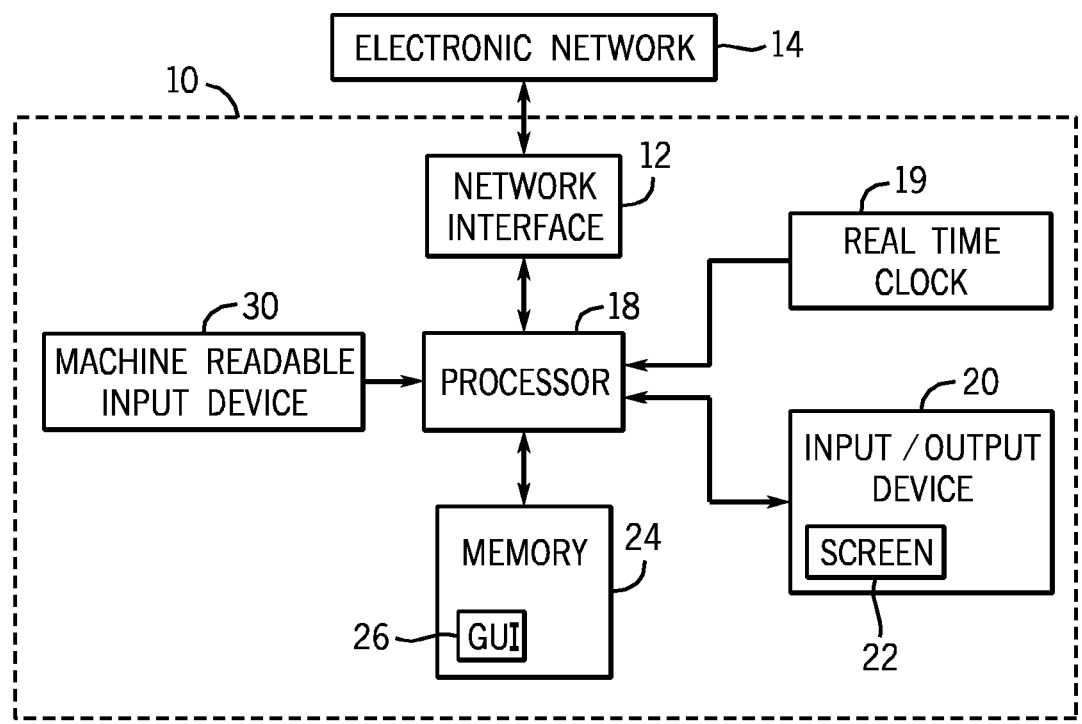
FIG. 1 illustrates a schematic diagram of a medical device according to the present invention.

While this invention is susceptible of embodiments in many different forms, there is shown in the drawings and will herein be described an example of the invention. The present disclosure is to be considered as an example of the principles of the invention. It is not intended to limit the broad aspect of the invention to the examples illustrated.

FIG. 1 is a schematic diagram illustrating several functional components of a medical pump 10 for implementing the present invention. Those of ordinary skill in the art will appreciate that the pump 10 includes many more components than those shown in FIG. 1. However, it is not necessary that all these components be shown in order to disclose an illustrative embodiment for practicing the present invention.

In the context of the present invention, the term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, or a diagnostic device.

Referring to FIGS. 2-13, for the purpose of exemplary illustration only, the medical device 10 is disclosed as an infusion pump. More particularly, the medical device 10 is a multi-channel infusion pump, a plurality of single or multi-channel infusion pumps in communication with or coupled to each other, or some combination thereof.

With reference to FIG. 1, the pump style medical device 10 includes a network interface 12 for connecting the medical device 10 to an electronic network 14. The electronic network 14 can be a completely wireless network, a completely hard-wired network, or some combination thereof. The device 10 may include an antenna (not shown) for wirelessly connecting to the electronic network 14. The antenna can project outside the device 10 or be enclosed within the housing of the device.

A processor 18 is included in the medical device 10 and performs various operations described in greater detail below. The input/output device 20 allows the user to receive output from the medical device 10 and/or input information into the medical device 10. Those of ordinary skill in the art will appreciate that input/output device 20 may be provided as a single device such as a touch screen 22, or as a separate display device and a separate input device (not shown), such as a keypad, keyboard, handheld or network computer. In one embodiment, the display screen 22 of the medical pump 10 is a thin film transistor active matrix color liquid crystal display with a multi-wire touch screen. The screen 22 measures approximately 8.5 in. (22 cm) diagonally and has a rectangular working area approximately 5 in. (13 cm) wide by 7 in. (18 cm) long. A membrane generally impermeable to fluids overlays the display screen 22 so the user can press on images of keys or buttons on the underlying screen with wet gloves, dry gloves or without gloves to trigger an input.

A memory 24 communicates with the processor 18 and stores code and data necessary for the processor 18 to perform the functions of the medical device 10. More specifically, the memory 24 stores multiple programs formed in accordance with the present invention for various functions of the medical device 10 including an infuser program that allows separate medication to be given to a patient from two or more channels in a specific manner.

The medical device 10 optionally includes a machine-readable input device 30 that addresses the problem of correctly performing a channel association when programming the medical device 10. The machine-readable input device 30 communicates with the medical device 10 to input machine-readable information to the medical device 10. The machine-readable input device 30 can communicate, directly or indirectly, with the medical device 10 via a wireless or hard-wired connection. The machine-readable input device 30 can be a device that is separate from, but associated or in communication with, the medical device 10.

The machine-readable input device 30 can be any sort of data input means, including those adapted to read machine-readable indicia, such as a barcode scanner or handheld personal digital assistant (PDA). Alternatively, the machine-readable input device 30 may be operable to read in other known forms of machine-readable information, such as radio frequency identification tags (RFID), touch memory, digital photography, biometrics, etc. For example, the device 30 can be a digital camera capable of generating an electronic image. In addition to assisting in channel association, such a device is useful for forming an electronic image of all or some portion of a drug container label.

Figure 2:
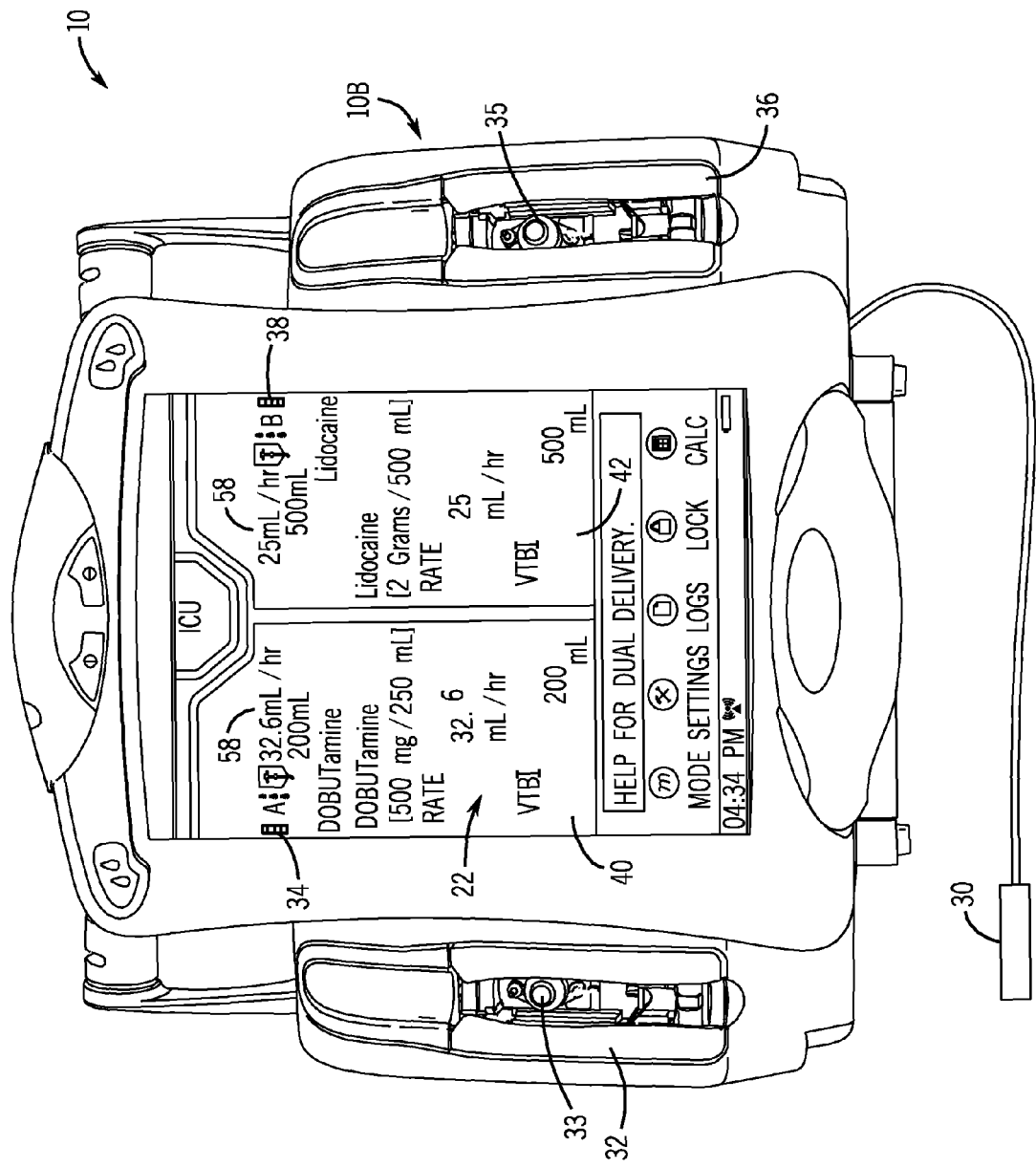
FIG. 2 is a front view of a multi-channel medical device according to the present invention.

With reference to FIG. 2, the medical device 10 is a multi-channel pump 10B having a first channel 32 and a second channel 36. A first tube set may be operably coupled to the first channel 32 to deliver a fluid from the first channel 32 and a second tube set may be operably coupled to the second channel 36 to deliver a fluid from the second channel 36. Each of the channels 32, 36 includes a respective pumping mechanism 33, 35 for acting upon a tube set to pump fluid. Various pumping mechanisms are well known in the art and the may be utilized without detracting from the present invention. Preferably, the tube set is made of soft, kink-resistant medical grade tubing and includes a conventional medicinal dispensing pump cassette that is acted upon by the pumping mechanism. The first channel 32 also includes a first channel machine-readable label 34 and the second channel 36 also includes a second channel machine-readable label 38. A user of the medical device 10 operates the machine-readable input device 30 to select a channel from one or more channels 32 and 36, by scanning in the associated machine-readable label 34 or 38.

The user selects the desired channel 32 or 36 by using the machine-readable input device 30 to scan a factory or hospital programmed, unique, machine-readable label 34 or 38 that is electronically generated and presented on the screen 22, preferably juxtapositioned near the respective channel 32 or 36. Alternatively, the machine-readable labels 34 and 38 are physically affixed to the medical device 10, preferably on or juxtapositioned near the channel 32 and 36, respectively. Since the machine-readable labels 34 and 38 are generated and/or can be stored in memory 24 by the pump 10B, the pump 10B can associate the machine-readable labels 34 and 38 to the channels 32 or 36. The pump 10B then allows the user to program and activate the selected channel 32 or 36. The user may also manually select the desired channel by touching an appropriate folder tab on the touch screen. The folder tabs are labeled and/or physically arranged on the screen so as to be proximate to the corresponding channel 32 or 36. That is, the "A" tab is juxtapositioned near or adjacent to the "A" channel 32 and the "B" tab is juxtapositioned near or adjacent to the "B" channel 36.

Figure 2A:
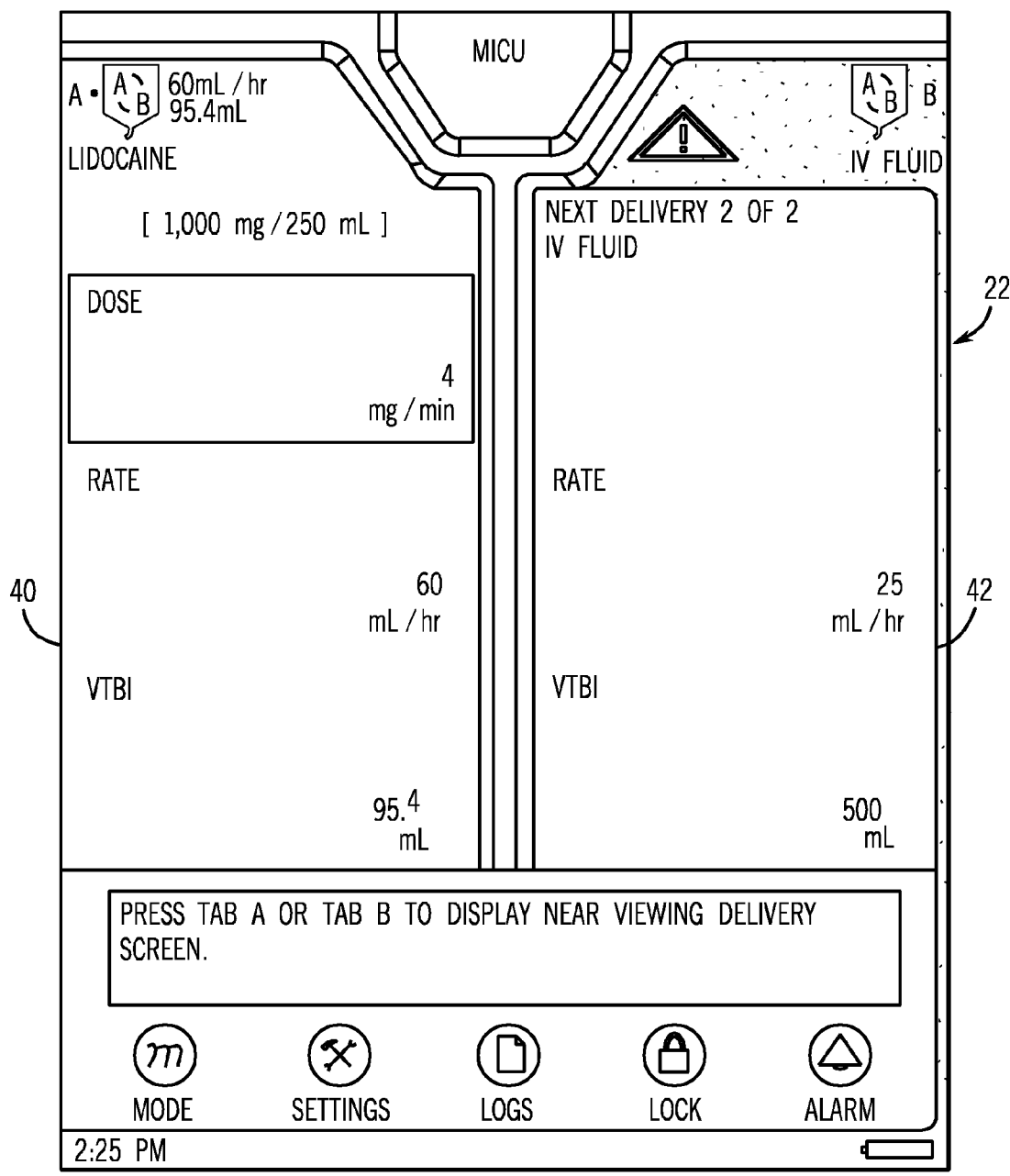
FIG. 2A is a screen shot of the multi-channel medical device of FIG. 2 programmed for interchannel sequence delivery according to the present invention.

With reference to FIGS. 1-2A, the graphical user interface program 26 reallocates screen 22 for a medical device 10. Specifically, FIG. 2 illustrates a multi-channel infusion pump 10B with a split touch screen 22 having a first channel screen portion 40 associated with first channel 32 and a second channel screen portion 42 associated with the second channel 36. Each channel screen portion 40 and 42 presents a subset of the delivery information regarding the respective channels 32 or 36, including without limitation therapeutic agent name, concentration, dose rate, VTBI, and alarm information, in a font size of at least twenty-eight points so that it is easily readable by a user from approximately fifteen to twenty feet (4.6-6.2 meters) away. This is what is referred to as a "far view" delivery screen.

When a user touches one of the tabs "A" or "B," or any part of the channel screen portions 40 or 42 of the far view delivery screen, a "near view" delivery screen is presented on the screen 22. The channel screen portion 40 or 42 selected or corresponding to the tab selected expands in area but the size of at least some of its text is reduced. The font size for rate and VTBI information on the near view delivery screen is substantially less than twenty-eight points. The other channel screen portion 40 or 42 (if present) is reduced in size, hidden or moved to the background to limit its space on the screen 22. Preferably, if the "A" tab of the first channel screen portion 40 is selected, the "B" tab of the second channel screen portion 42 remains exposed, but is grayed or colored differently to indicate it is not the channel of interest. Thus, the second channel screen portion 42 becomes smaller than the first channel screen portion 40, as the first channel screen portion 40 is currently being viewed and adjusted by the user and is therefore of primary concern. The second or B channel can be selected in a similar manner, whereupon the first channel portion 40 of the screen 22 will become smaller and the second channel portion 42 will become larger. Since the screens for the respective channels are substantially identical, except for the position of their tabs 58, features shown in the drawings and described below relative to the A channel also apply to the B channel, and vice versa.

Figure 3:
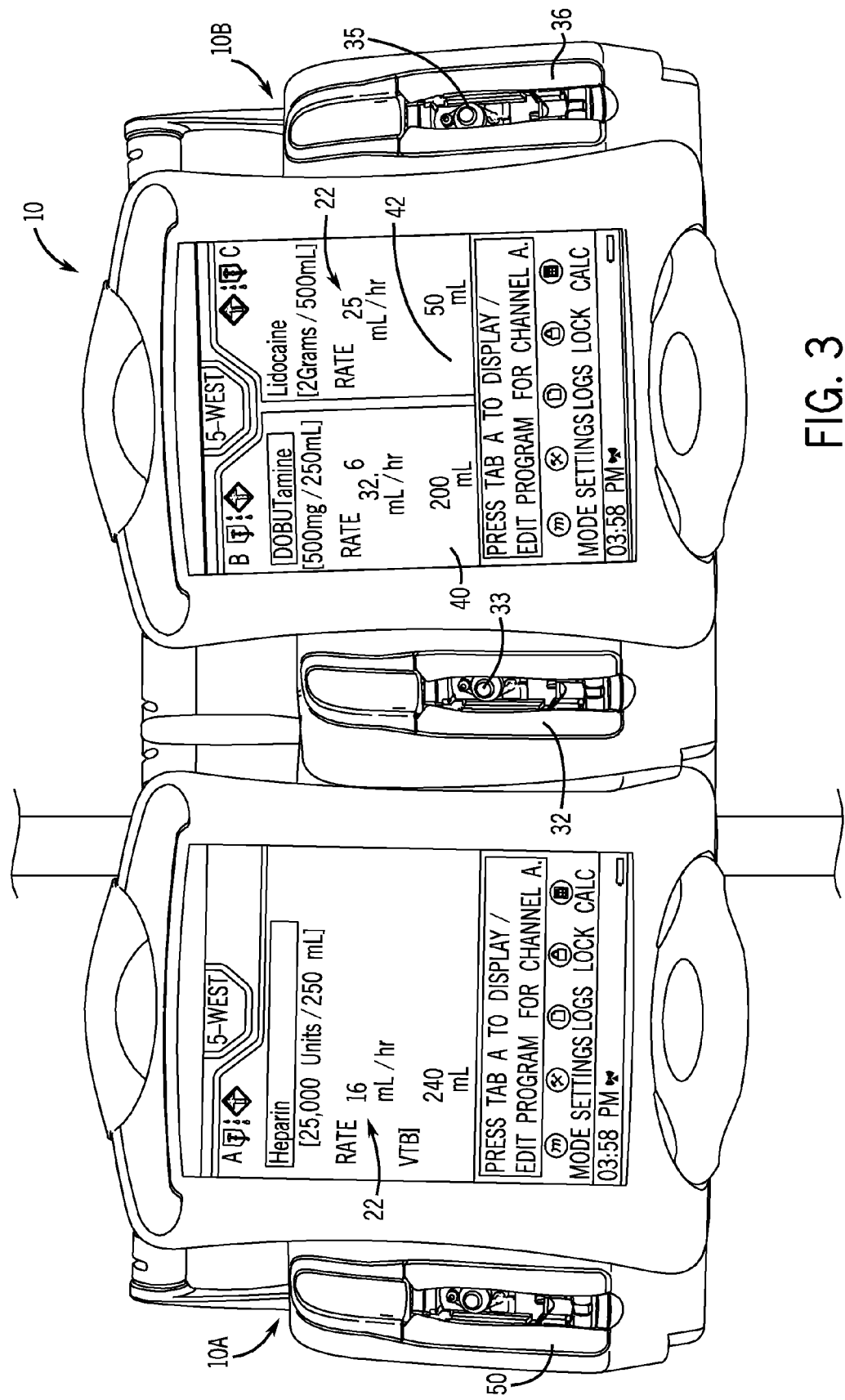
FIG. 3 is a front view of two medical devices associated with one another having displays according to the present invention; and, FIG. 4-FIG. 13 illustrate screen shots of the infuser system, method, and computer program according to the present invention.

FIG. 3 illustrates a multi-channel infusion pump 10B having a first or A channel 32 and a second or B channel 36 and a single channel infusion pump 10A having a third or C channel 50. The multi-channel infusion pump 10B and the single channel infusion pump OA are physically and communicatively connected to each other for programming and operation in a coordinated manner. In one example, the multi-channel infusion pump 10B and the single channel infusion pump 10A are detachably coupled together. Although FIG. 3 illustrates a single channel medical device 10A associated with a multi-channel medical device 10B, is it noted that this is for illustrative purposes only, and other various combinations of multiple medical devices 10 may be made without departing from the present invention. Additionally, while the medical devices 10A and 10B are shown as being physically associated, it is contemplated that they may alternatively be wirelessly associated.

The features and functions of the graphic user interface program 26 and medical device 10 are further described in U.S. Patent Application Publication No. 2006/0229557 entitled "User Interface Improvements for Medical Devices," which is fully incorporated by reference herein.

As described above, the memory 24 stores multiple programs formed in accordance with the present invention, including an infuser program that allows for interchannel sequencing therapy. Interchannel sequencing therapy allows for the sequential delivery of separate medication from two or more channels. In particular, the infuser program can be programmed by a user to sequence medication dispensation between channels such that a patient can receive medication from two or more channels without having to reprogram the infusion pump 10.

Figure 4:
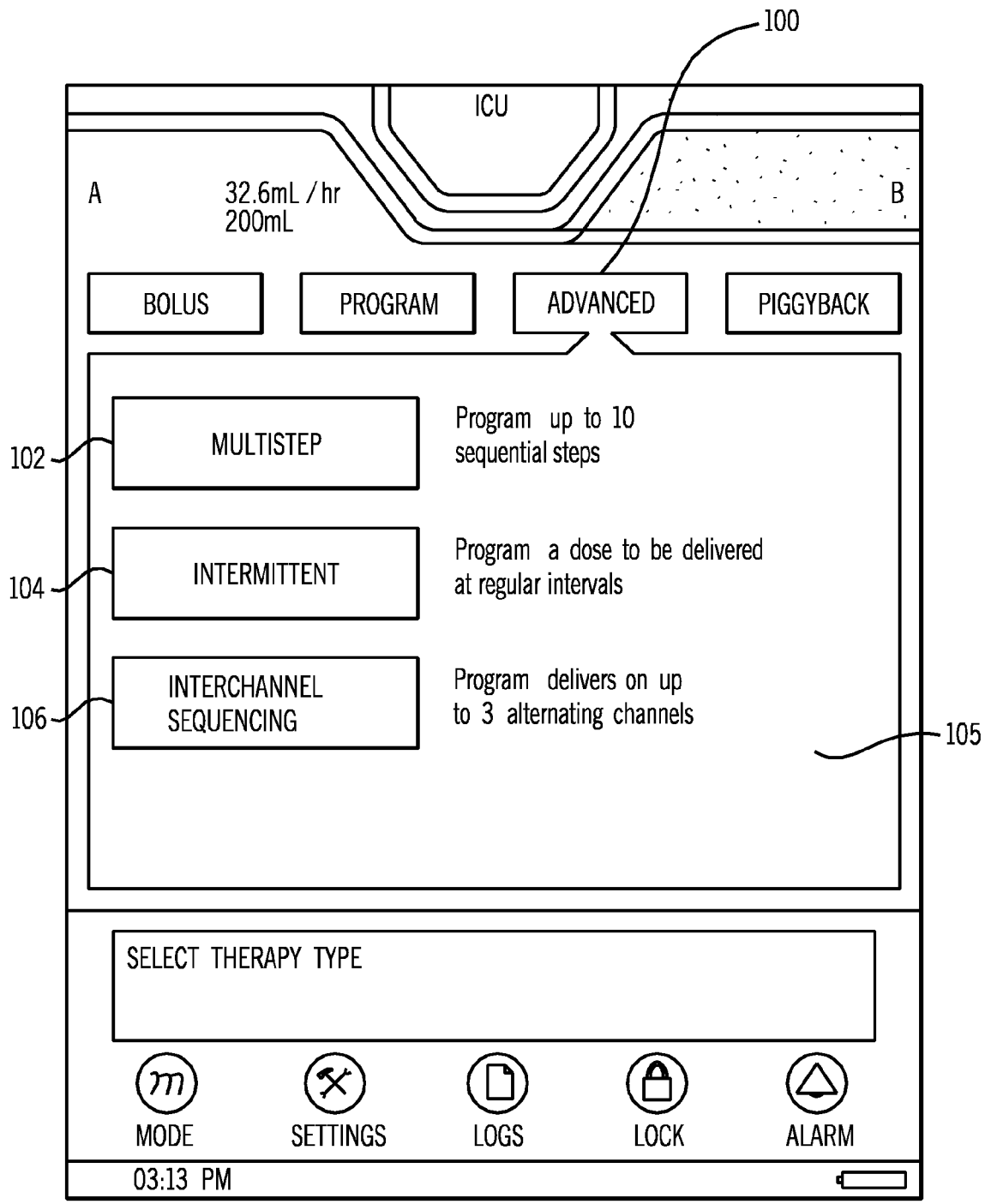

FIG. 4 illustrates the selection screen from which a user can select to program the infusion pump 10 to deliver an interchannel sequencing therapy. In one example, the selection screen can be displayed on the touch screen 22 of the infusion pump. However, it is also contemplated that the selection screen can be displayed on a screen that is remote from the infusion pump 10, such as a computer monitor located at a nurses' station, and from which the user remotely programs the infusion pump 10. Further, when multiple infusion pumps are coupled together, as illustrated in FIG. 3, channels on multiple pumps may be programmed from the interface of one of the pumps.

Figure 5:
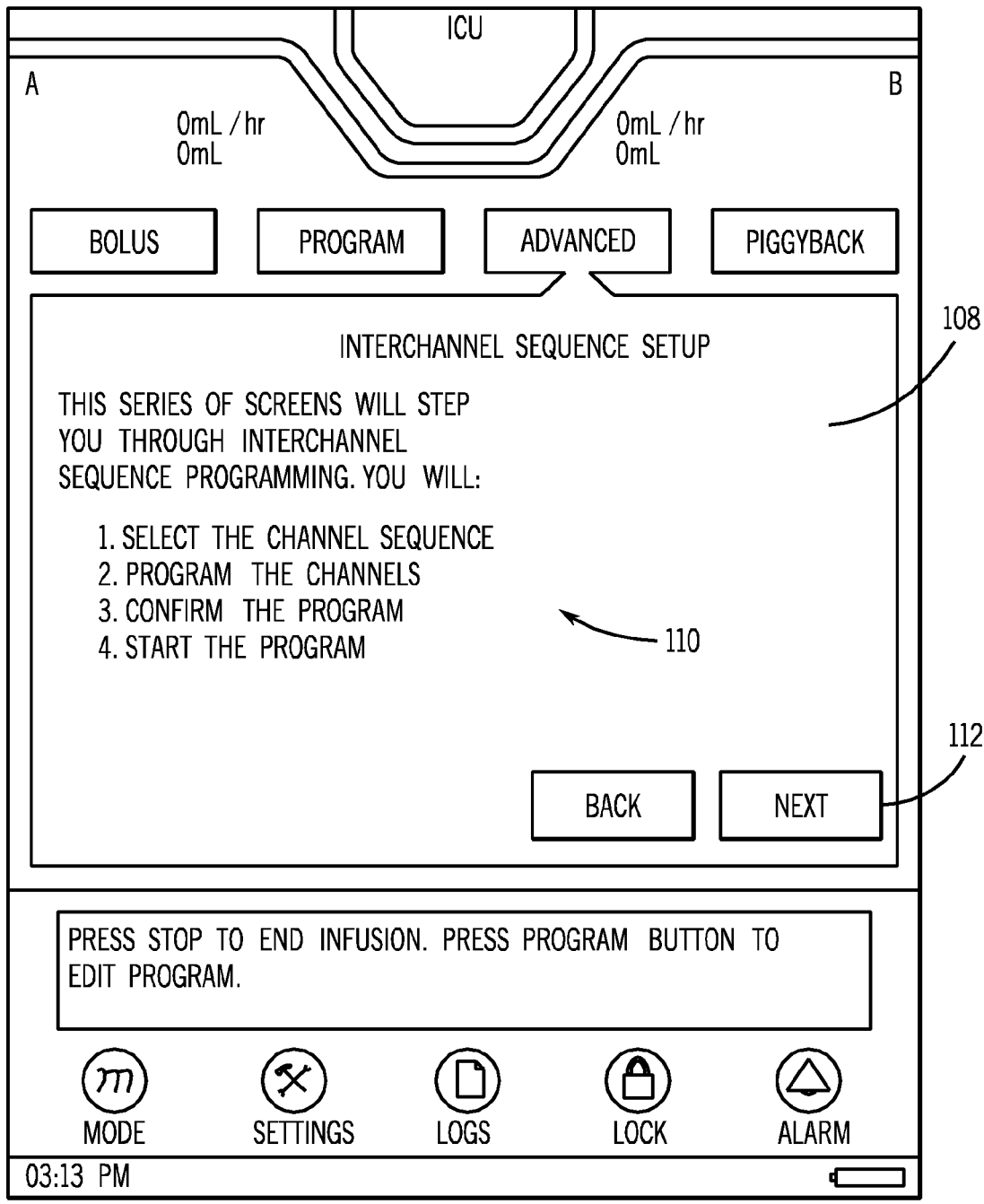

With reference to FIG. 4, the user selects the "Advanced" tab 100 which provides for the option to deliver complex therapy infusions to the patient. In one example, the "Advanced" tab 100 may be displayed on screen 105 which allows the user to select from "Multistep" therapy button 102, "Intermittent" therapy button 104, and "Interchannel Sequencing" therapy button 106. In order to select the "Interchannel Sequencing" therapy, the user may touch the portion of the screen 22 on which the "Interchannel Sequencing" therapy button 106 is located. Once the "Interchannel Sequencing" therapy button 106 is selected, the Interchannel Sequence Setup Introduction screen 108 is displayed, as illustrated in FIG. 5.

Preferably, the Interchannel Sequence Introduction screen 108 provides an outline of the steps taken to program and administer the interchannel sequencing therapy. For example, the Setup screen 108 may include text 110 which informs the user that the following steps will be taken: (1) Select the channel sequence; (2) Program the channels; (3) Confirm the program; and, (4) Start the program. Upon selecting the "Next" button 112, a modified Interchannel Sequence Setup screen 114 appears, as illustrated in FIG. 6.

Figure 6:
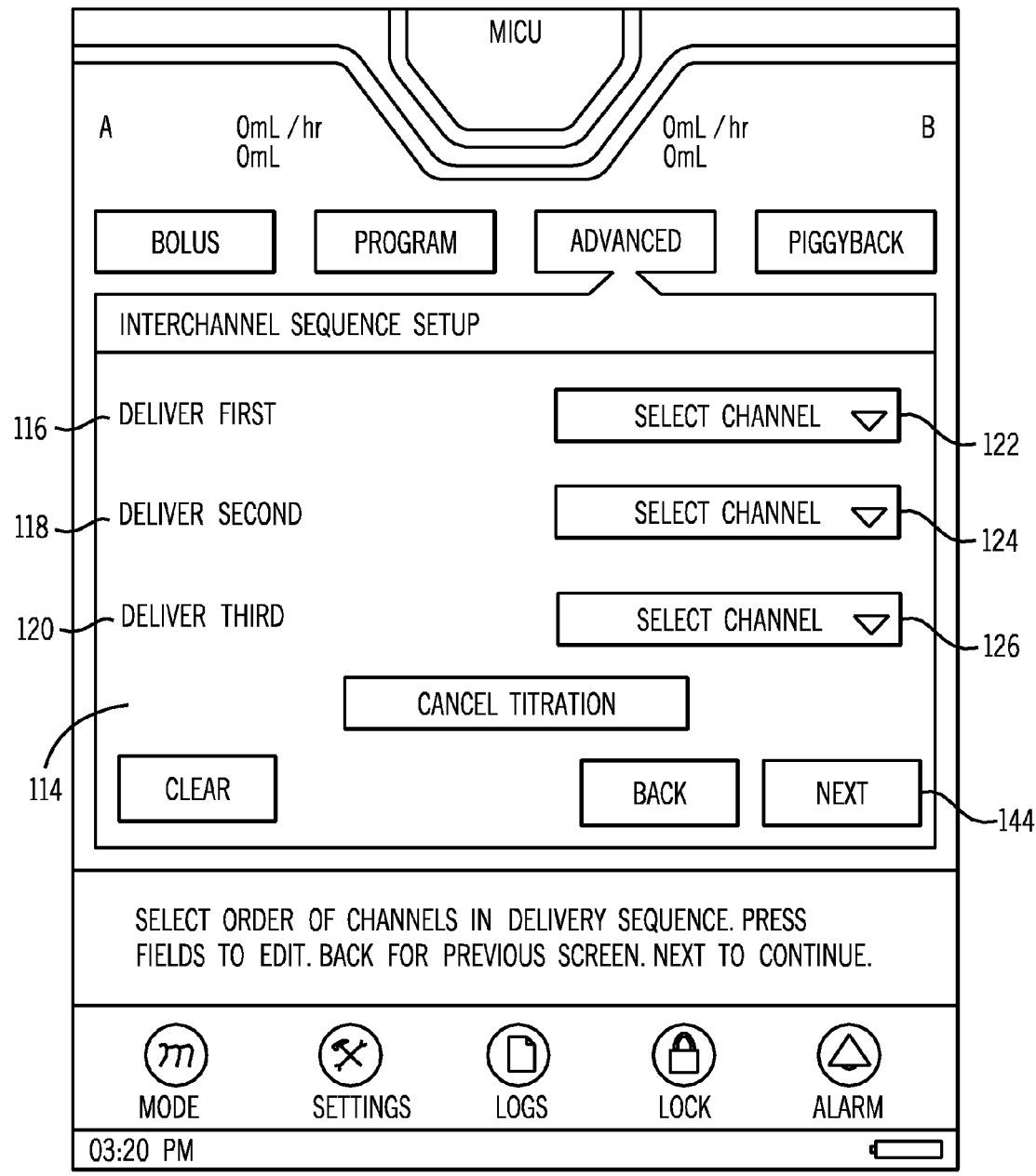

The Interchannel Sequence Setup screen 114 of FIG. 6 allows the user to input channel sequence data which identifies the sequence of delivering fluid from the infusion pump channels. As noted above, the channels from which fluid will be delivered can be located on a single infusion pump 10 or on multiple infusion pumps 10A, 10B that are in communication with each other. As illustrated in FIG. 6, the Setup screen 114 allows the user to identify the channel sequence by selecting which channel to "Deliver First" 116, "Deliver Second" 118, and "Deliver Third" 120. Although FIG. 6 illustrates that the sequence may be programmed for three deliveries, this is for illustrative purposes only, and it is contemplated that the sequence may be programmed to include any number of deliveries from any number of infusion pumps.

Figure 7:
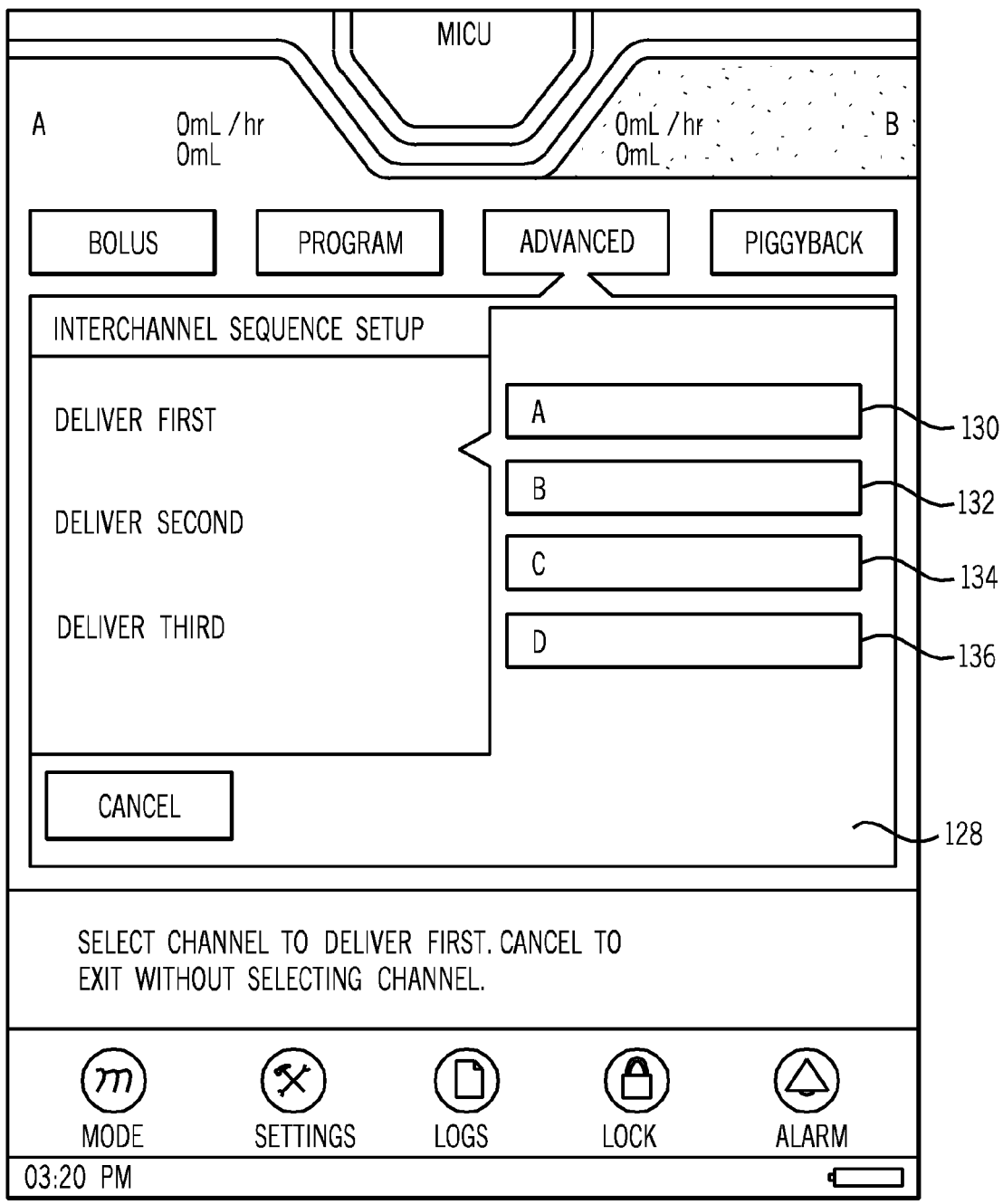

In particular, the user selects the appropriate channel in the field 122, 124, 126 next to the respective delivery sequence identification to identify which channel should be delivered. For example, if the user selects the "Select Channel" field 122 for Deliver First 116, the user is presented with a Channel Selection screen 128, as illustrated in FIG. 7. The Channel Selection screen 128, illustrated in FIG. 7, allows the user to specify which channel should be delivered first by selecting the appropriate channel identification. Again, although FIG. 7 illustrates that user may select "A" 130, "B" 132, "C" 134, and "D" 136, it is contemplated that any number of channels may be used in the system, and any of those may be selected from the Channel Selection screen 128. Once the user selects the appropriate channel from which to deliver fluid first, the user is presented with the Setup screen 114 illustrated in FIG. 8A.

Figure 8A:
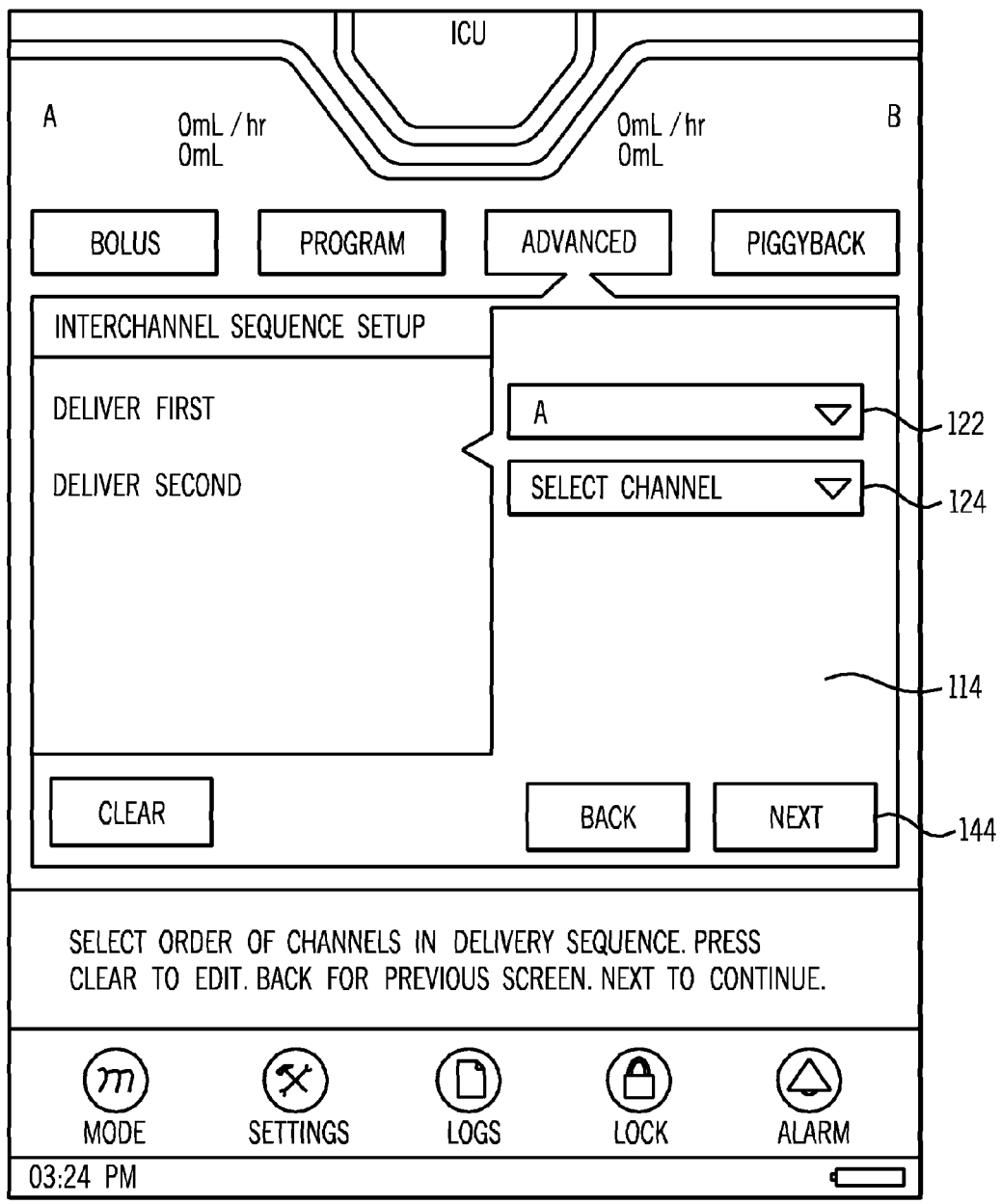
Figure 8B:
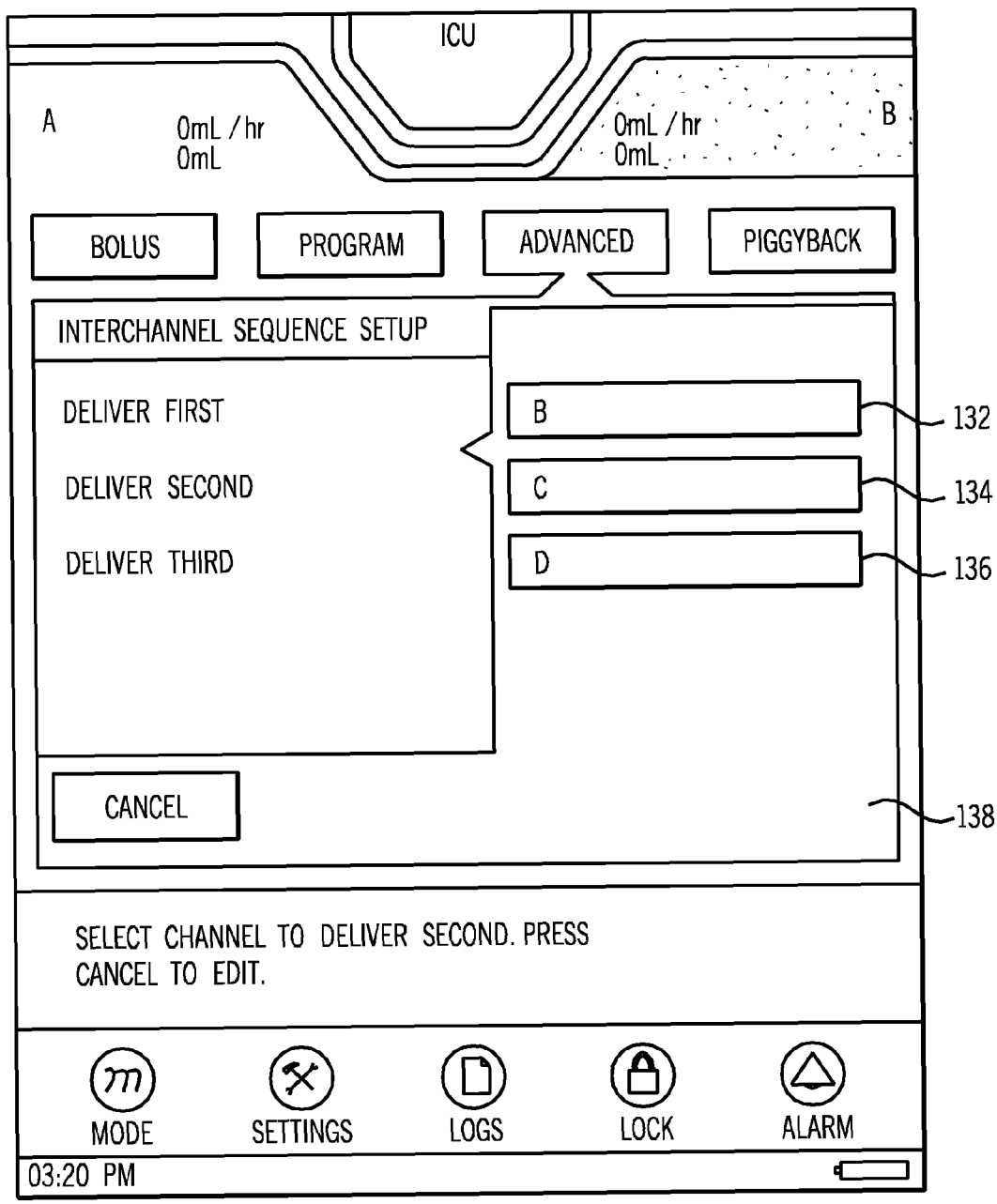

After the user selects which channel from which to first deliver fluid, the user selects the next channel in the sequence from which to deliver fluid. With reference to FIG. 8A and FIG. 8B, the user selects the channel field 124 that corresponds to "Deliver Second" 118. Upon selecting the channel field 124 that corresponds to "Deliver Second" 118, the user is presented with Channel Selection screen 138, as illustrated in FIG. 8B. The Channel Selection screen 138, illustrated in FIG. 8B, allows the user to specify which channel should be delivered second by selecting the appropriate channel identification. In one example, the channel which is selected in the field 122 corresponding to Deliver First 116, i.e., channel A, is not available to be selected in the Channel Selection screen 138 for the Deliver Second 118. Therefore, the user may select from "B" 132, "C" 134, and "D" 136. Again, it is contemplated that any number of channels may be used in the system, and any of those may be selected from the Channel Selection screen 138.

Upon selecting the appropriate channel from which to deliver fluid second, the user is again presented with the Setup screen 114 of FIG. 6. The user may continue to program delivery sequence by selecting additional channel fields to identify the sequence and channels from which to deliver fluid. The particular channel selected in the field corresponding to the delivery immediately prior to the currently selected delivery is typically not shown. However, a channel which has previously been selected for a delivery that does not immediately precede the currently selected delivery may be shown. For example, as illustrated in FIGS. 6-8B and as described above, because channel A is selected for first delivery, it is not presented as an option for second delivery. Similarly, if channel B is selected for second delivery, it is not presented as an option for third delivery. However, channel A may be presented as an option for third delivery because it was not selected for the delivery which immediately precedes the third delivery, i.e., the second delivery. Thus, in this example, first delivery is from channel A, second delivery is from channel B, and third delivery is from channel A.

Figure 9:
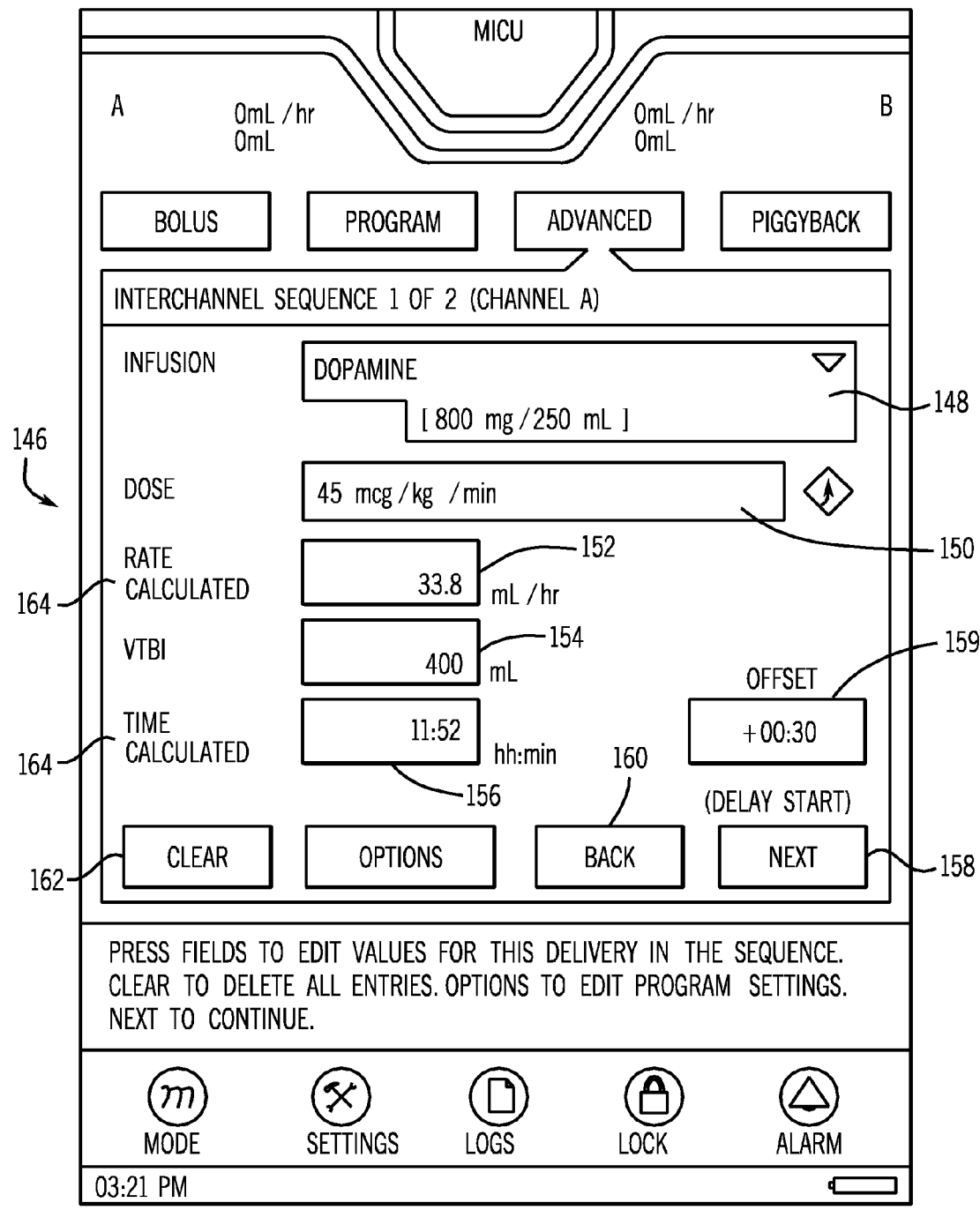

After the user has inputted the desired channel sequence data, the user can select the Next button 144 on the Interchannel Sequence Setup screen 114 of FIG. 6, to display the delivery data screen 146 of FIG. 9 on the screen 22. The delivery data screen 146 allows the user to input delivery data for each of the selected channels. The processor 18 controls delivery from each of the identified channels according to the inputted delivery data. As illustrated in FIG. 9, the delivery data screen 146 identifies the sequence and the channel from which the infusion will occur. For example, the delivery data screen 146 illustrated in FIG. 9 identifies the first channel from which fluid will be delivered by displaying "Interchannel Sequence 1 of 2 (Channel A)". The delivery data screen 146 allows the user to input delivery data such as, fluid identification data 148, dosage data 150, rate data 152, fluid volume data 154, and delivery time data 156 for the first delivery. A time offset 159 may also be input as described below. The delivery data screen 146 also includes a Back button 160 that allows the user to view the Interchannel Sequence Setup screen 114.

The fluid identification data 148 identifies the type of fluid which is to be infused from the selected channel, such as Dopamine [800 mg/250 mL]. The dosage data 150 identifies the dose which is to be delivered, such as 45 mcg/kg/min. The dosage rate 150 can be preprogrammed in the infusion pump, or the user or a bar code point of care system may enter the dosage rate 150. The fluid volume data 154 identifies the total volume of fluid that is to be infused, such as 400 mL. Based on the fluid identification data 148, the dosage data 150, and the fluid volume data 154, the infuser program calculates the rate data 152 which indicates the rate of infusion and the delivery time data 156 which indicates the total time to complete infusion for the first delivery. Alternatively, the rate data 152 and delivery time data 154 may be inputted by the user. In such a situation, the infuser program calculates the fluid volume data 154. The delivery data screen 146 also includes a Clear button 162 that allows the user to clear the inputted delivery data and repeat the above described process. In either embodiment, the delivery data screen 146 may identify which data is calculated by the system by including a textual identification 164, such as "(calculated)". Anytime two out of the three variables dose rate, volume, and time are known, the processor 18 can calculate the third. When dosage is weight based, the dose rate can be calculated based on a known or input patient weight and the dosage. The time counts down as the programmed infusion progresses.

Figure 10:
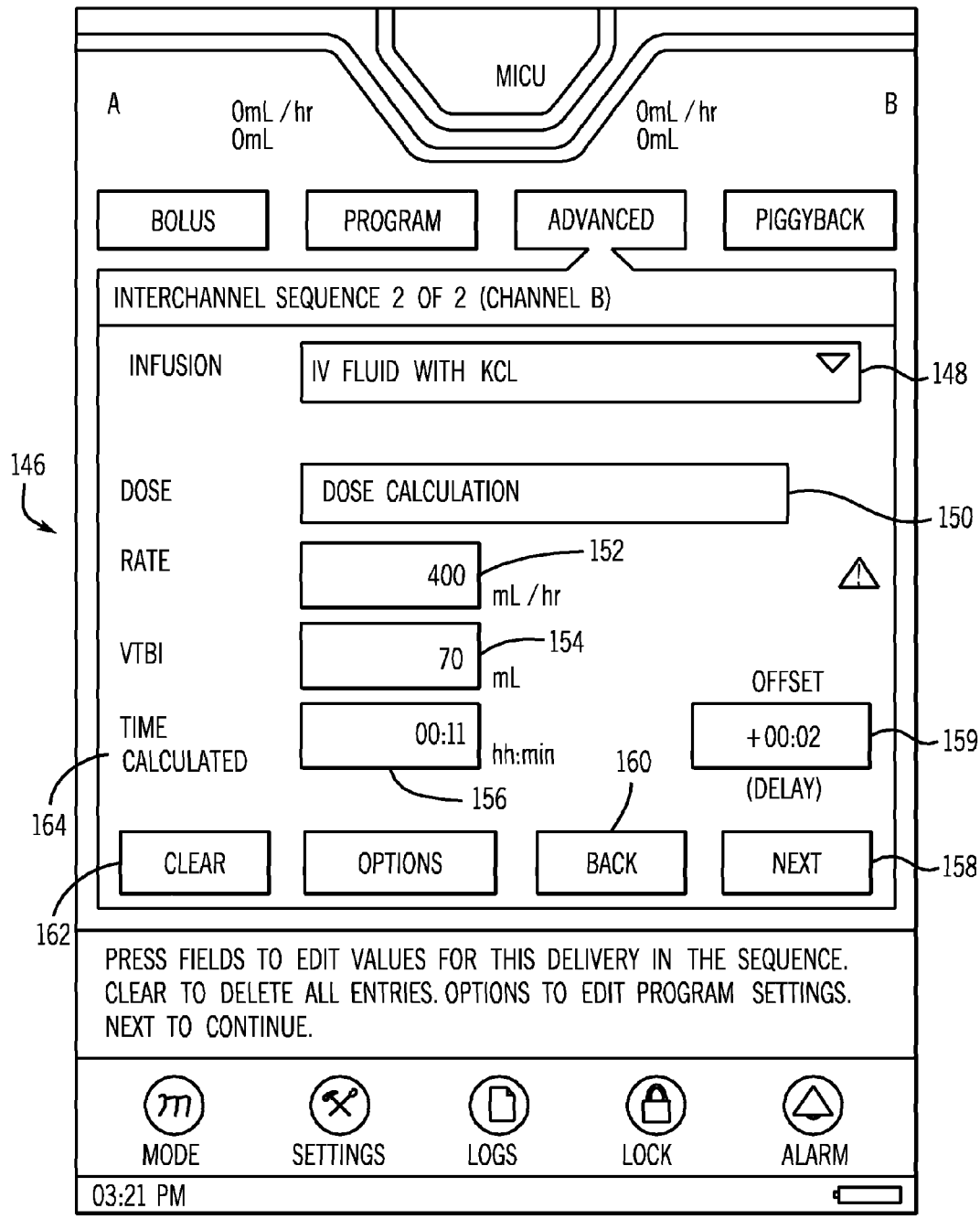

After inputting the delivery data for the first delivery, the user can select the Next button 158 to display the delivery data screen 146 for the second channel from which fluid will be delivered. As illustrated in FIG. 10, the delivery data screen 146 identifies the second channel from which fluid will be delivered by displaying, "Interchannel Sequence 2 of 2 (Channel B)." It is contemplated that the infuser program can be programmed to deliver fluid from the second channel immediately after the first delivery has been completed. It is also contemplated that by using a real time clock 19 (FIG. 1) associated with the processor 18 the infusion program can be programmed to deliver fluid from the first channel and the second channel concurrently (with total or partial overlap) or sequentially with a delay. A time offset 159 can be inputted by the user. With the addition of a +/−key to the touch screen keypad shown in FIG. 5L of US2006/0229557, the time offset 159 can be input as a positive, zero or negative value, typically in units of hours and/or minutes. Inputting a positive value for the time offset 159 will cause a delay in the start of the particular fluid delivery. This can be particularly useful in avoiding undesirable drug-drug interactions. Inputting a zero value for the time offset 159 will cause the delivery to start immediately after "confirmation" and "start" buttons are pressed for the first delivery or immediately (with no delay or time gap) after the preceding delivery in the case of subsequent deliveries. Inputting a negative value will cause concurrent delivery, with the second delivery starting the specified number of hours and/or minutes before the end of the preceding delivery. One skilled in the art will appreciate that the time offset 159 can be inputted either as delivery data, as illustrated by FIGS. 9 and 10, or included as additional channel sequence data in FIGS. 6-8B. As with the data delivery screen 146 for the first delivery illustrated in FIG. 9, the delivery data screen 146 for the second delivery of FIG. 10 allows the user to input delivery data such as, fluid identification data 148, dosage data 150, rate data 152, fluid volume data 154, and delivery time data 156 for the second delivery. The delivery data screen 146 also includes a Back button 160 that allows the user to view the delivery data screen 146 for the first delivery (illustrated in FIG. 9). The delivery data screen 146 for the first delivery also includes a Back button 160 that allows the user to view the Interchannel Sequence Setup screen 114.

As illustrated in FIG. 10, the fluid identification data 148 identifies the type of fluid which is to be infused from the selected channel, such as IV Fluid with KCL (potassium chloride), the rate data 152 identifies the rate at which the fluid is dispensed, such as 400 mL/hr, and the fluid volume data 154 identifies the total volume of fluid that is to be infused, such as 70 mL. Based on the rate data 152 and the fluid volume data 154, the infuser program calculates the fluid delivery time data 156 which indicates the total time to complete infusion for the second delivery. Alternatively, the rate data 152 and fluid delivery time data 156 may be inputted by the user and the infuser program calculates the fluid volume data 154 based on these inputs. The delivery data screen 146 also includes a Clear button 162 that allows the user to clear the inputted delivery data and repeat the above described process.

Figure 11A:
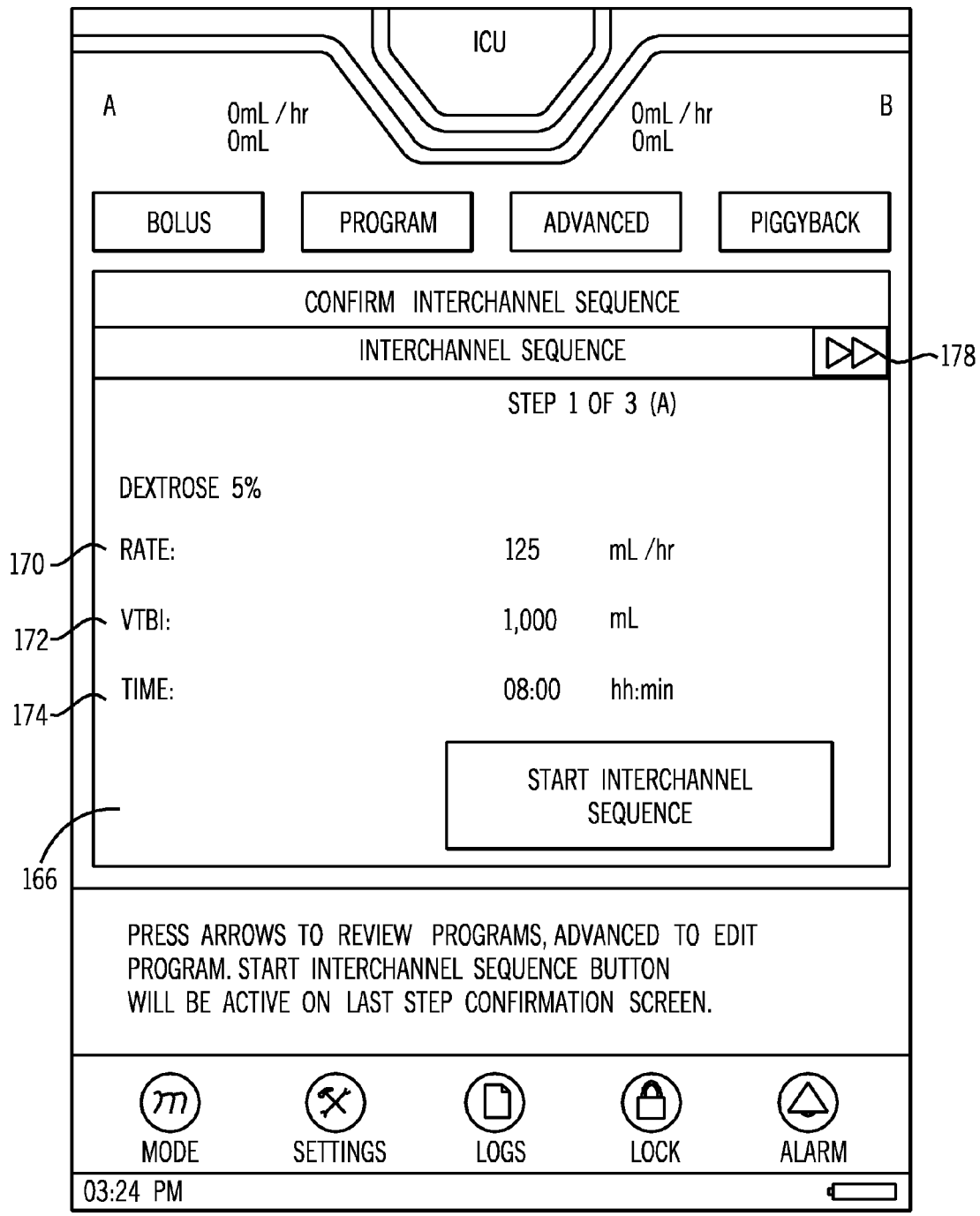
Figure 11B:
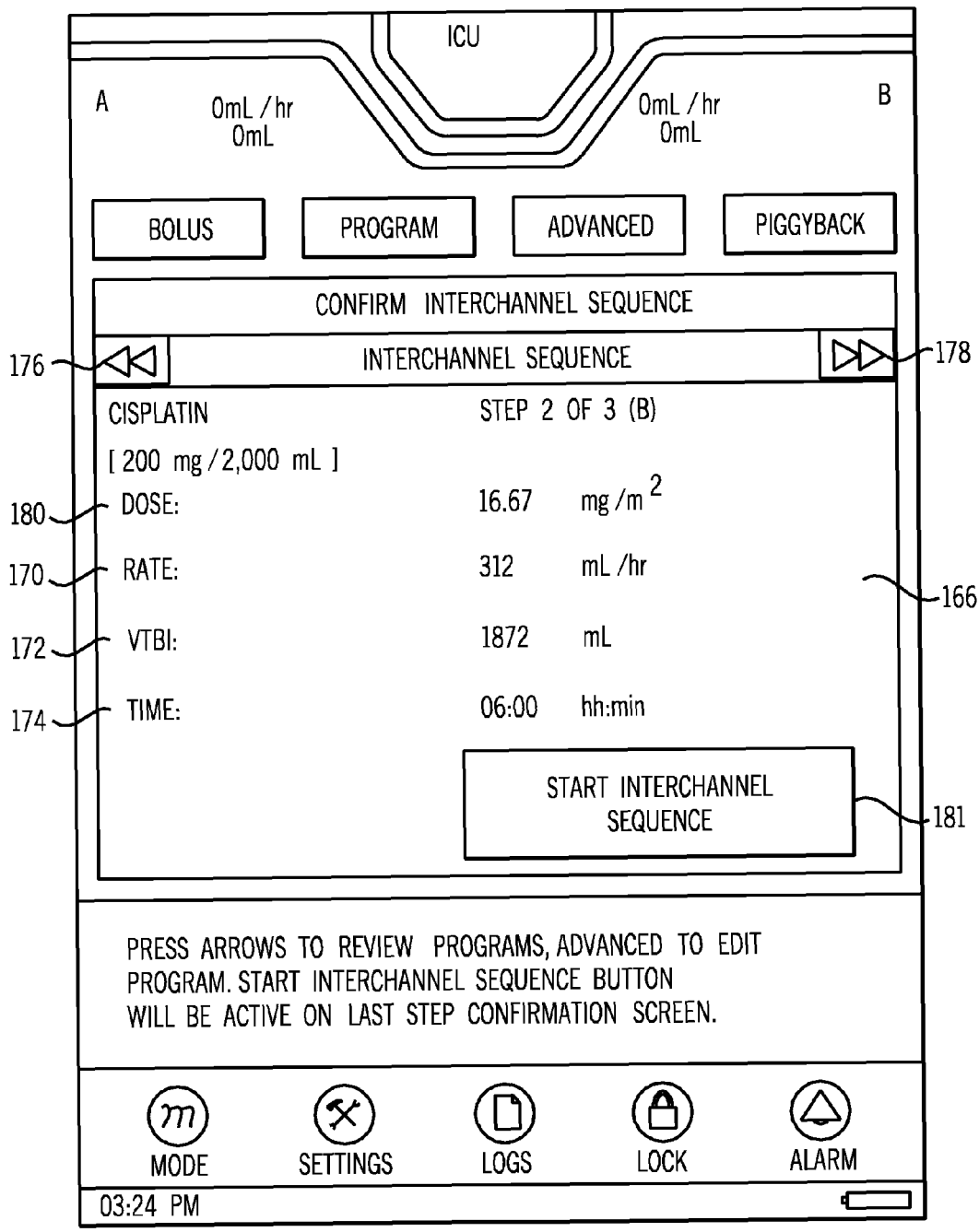

After inputting the delivery data for the second delivery, the user can select the Next button 158 to display the delivery data screens 146 for subsequent channels from which fluid will be delivered. The delivery data screens for the subsequent channels are similar to the delivery data screens 146 for the first and second deliveries and include the similar delivery data inputs. Once all delivery data has been entered, the user can select the Next button 158 to display a confirmation screen 166, as illustrated in FIG. 11A and FIG. 11B. FIG. 11A illustrates the confirmation screen 166 including delivery data for the first channel which is scheduled to be delivered. For example, the confirmation screen 166 may display the fluid to be infused 168, the rate of infusion 170, the volume to be infused 172, and the total time for infusion 174 from the first channel.

The confirmation screen 166 may include a left horizontal scroll button 176 (FIG. 11B) and a right horizontal scroll button 178 which allow a user to scroll through and review each delivery for the interchannel sequence therapy. For example, if the user selects the right scroll button 178, the confirmation screen 166 for the second delivery is displayed, as illustrated in FIG. 11B. The confirmation screen 166 includes delivery data for the second delivery, including the fluid to be infused 168, the dosage 180, the rate of infusion 170, the volume to be infused 172, and the total time for infusion 174 from the second channel. The user may re-review the confirmation screen for the first delivery by selecting the left horizontal scroll button 178.

The user may continue to select the right horizontal scroll button 178 to view delivery data for additional deliveries that have been scheduled. Preferably, selecting the right horizontal scroll button 178 selects the delivery that is scheduled subsequent to the delivery that is presently displayed on the screen 22. Similarly, selecting the left scroll button 178 selects the delivery that is scheduled immediately prior to the delivery that is displayed on the screen 22. However, those of ordinary skill in the art will appreciate that other methods of reviewing confirmation screens for multiple deliveries may be used.

After reviewing the confirmation screen 166 for the scheduled deliveries, the user may select the Start Interchannel Sequence button 180 to begin the infusion therapy to deliver fluid in accordance with the channel sequence data and the delivery data for the respective channel being delivered. In the example of FIG. 4-FIG. 11, fluid is delivered first from channel A in accordance with the delivery data for the first delivery. After fluid delivery from channel A is completed, fluid is delivered from channel B in accordance with the delivery data for the second delivery. The infusion pump need not be stopped, paused, or reprogrammed between the first delivery and the second delivery. Instead, the infusion pump controls the infusion of fluid from all channels, without user intervention.

Figure 12:
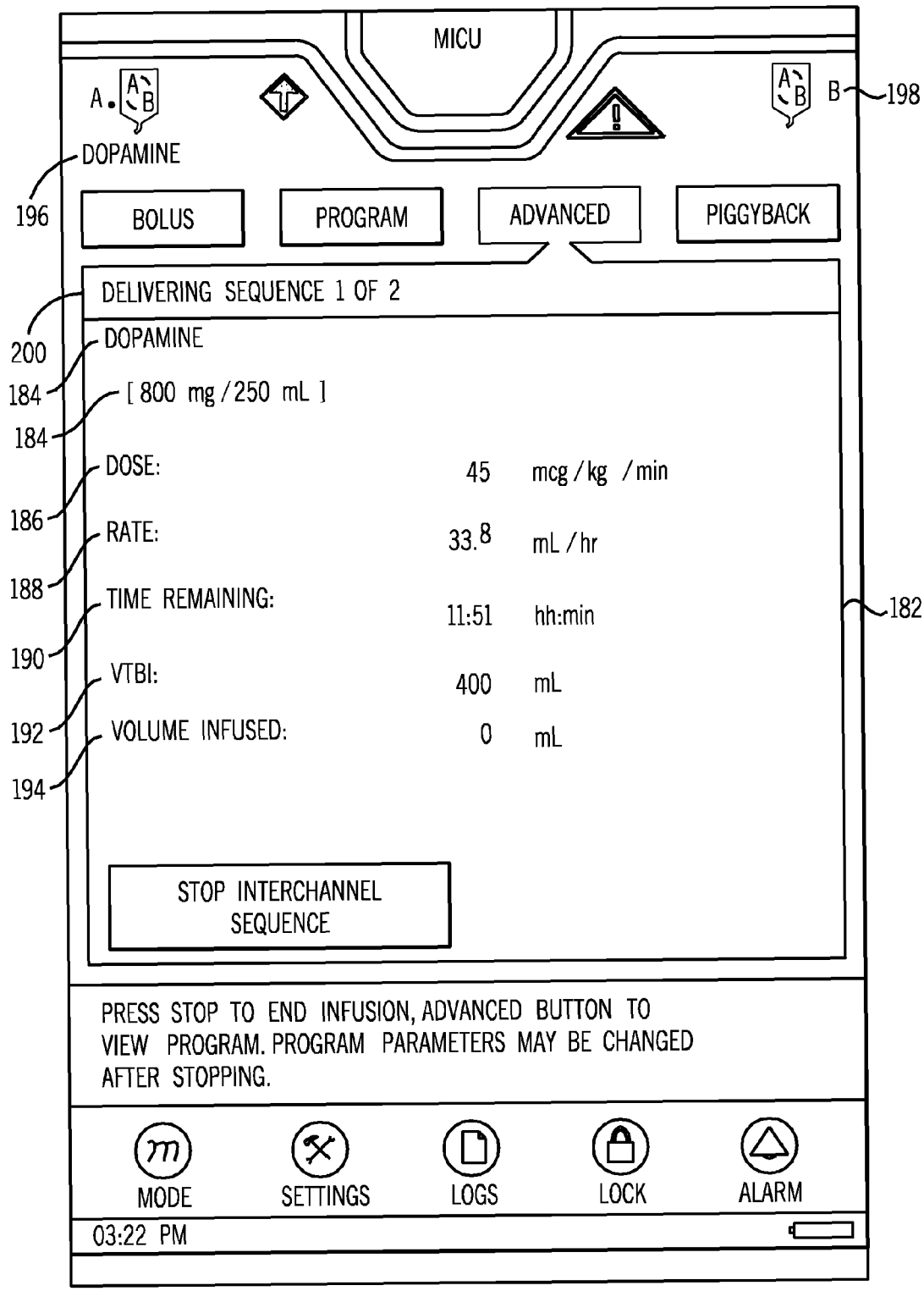

During the infusion delivery, a Status screen 182 is displayed on the screen 22, as illustrated in FIG. 12. The Status screen 182 displays infusion data corresponding to the channel from which fluid is currently being delivered. The infusion data may include fluid identification data 184, dosage data 186, rate data 188, delivery time remaining data 190, fluid volume data 192, and volume delivered data 194. For example, as illustrated in FIG. 12, the fluid identification data 184 may be DOPamine [800 mg/250 mL], the dosage data 186 may be 45 mcg/kg/min, the rate data 188 may be 33.8 mL/hr, the delivery time remaining data 190 may be 11:51 hh:mm, the fluid volume data 192 may be 400 mL, and the volume delivered data 194 may be 0 mL. The Status screen 182 also includes sequence data 200 which indicates the delivery that is currently being delivered. For example, the sequence data 200 may indicate that the infusion pump 10 is delivering sequence 1 of 2.

The Status screen 182 of FIG. 12 also includes a first delivery channel tab 196 and a second delivery channel tab 198 which identifies the channel and the fluid that will be delivered for the particular delivery. For example, the first delivery channel tab 196 may indicate that DOPamine will be delivered from channel A and the second delivery channel tab 198 may indicate that IV fluid with KCL will be delivered from channel B.

Figure 13:
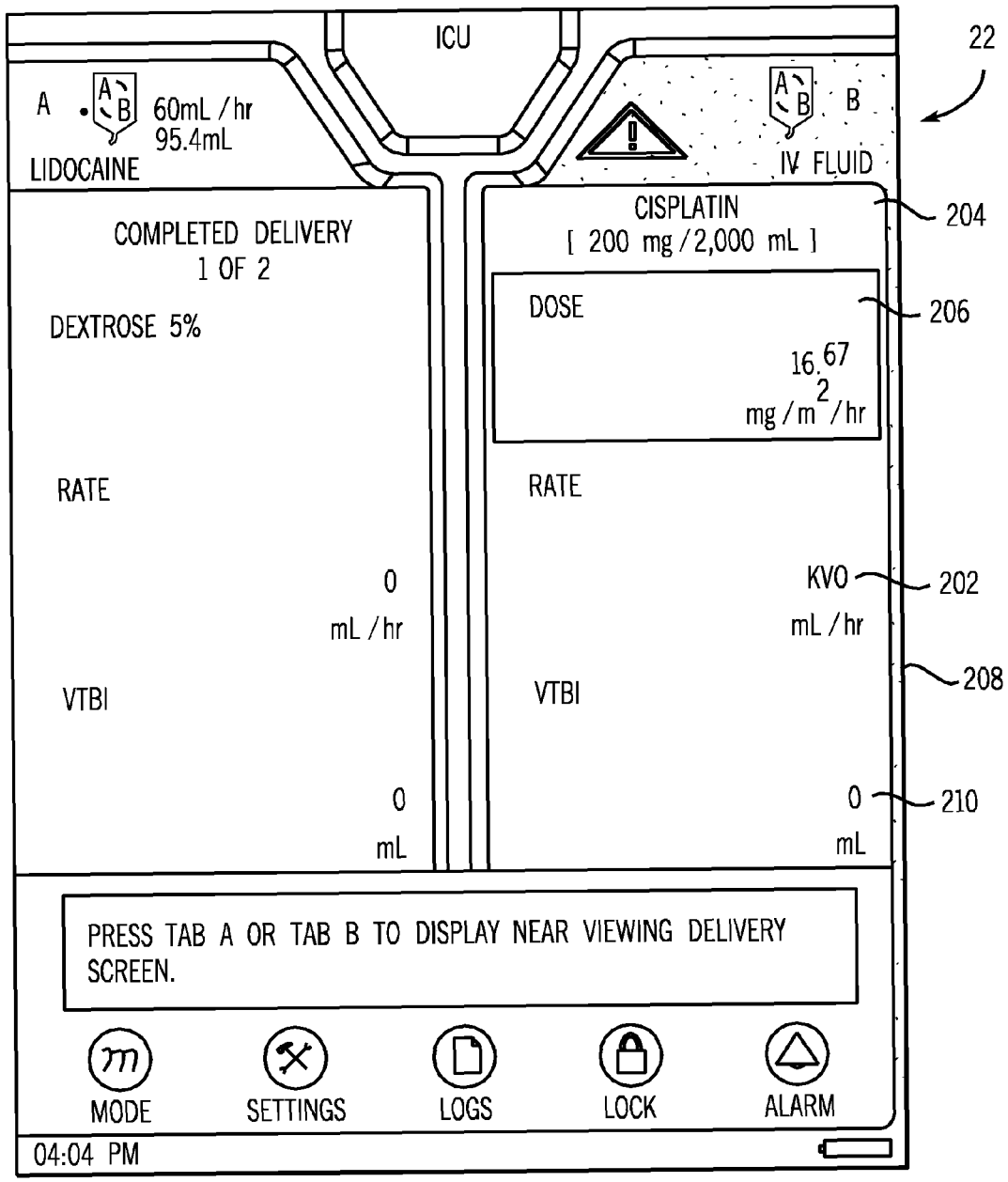

The infuser program also allows, separately or as part of interchannel sequence programming, the infusion pump to be programmed to permit a keep vein open (KVO) therapy that delivers KVO fluid after the interchannel sequencing therapy infusion is completed. The KVO therapy prevents the vein from closing by delivering a fluid, such as Cisplatin, to the patient. The KVO therapy is delivered only after the last fluid programmed for the interchannel sequencing therapy is delivered. During the KVO therapy, a KVO therapy screen 202 may be displayed on the screen 22, as illustrated in FIG. 13. The KVO therapy screen 202 may display KVO fluid delivery data. The KVO fluid delivery data may include KVO fluid identification data 204, dosage data 206, rate data 208, and fluid volume data 210.

While the foregoing has described what are considered to be the best mode and/or other examples, it is understood that various modifications may be made therein and that the subject matter disclosed herein may be implemented in various forms and examples, and that they may be applied in numerous other applications, combinations and environments, only some of which have been described herein. Those of ordinary skill in that art will recognize that the disclosed aspects may be altered or amended without departing from the true spirit and scope of the subject matter. Therefore, the subject matter is not limited to the specific details, exhibits and illustrated examples in this description. It is intended to protect any and all modifications and variations that fall within the true scope of the advantageous concepts disclosed herein.

We claim:

1. A method for controlling at least one infusion pump, the method comprising:

inputting channel sequence data into a processor in electronic communication with the at least one infusion pump, wherein the channel sequence data identifies a sequence for delivering a first fluid from a first channel and a second fluid from a second channel; and then inputting into the processor first delivery data for the first channel and second delivery data for the second channel; and, delivering the first fluid from the first channel and second fluid from the second channel according to the inputted channel sequence data, the first delivery data, and the second delivery data.

2. The method of claim 1 wherein the first channel and the second channel are located on a single infusion pump.

3. The method of claim 1 wherein one of the second delivery data and the channel sequence data identifies that the first fluid from the first channel and the second fluid from the second channel will be delivered according to a time offset.

4. A method for controlling at least one infusion pump, the method comprising:

inputting channel sequence data into a processor in electronic communication with the at least one infusion pump, wherein the channel sequence data identifies a sequence for delivering a first fluid from a first channel and a second fluid from a second channel; and then inputting into the processor first delivery data for the first channel and second delivery data for the second channel; and delivering the first fluid from the first channel and second fluid from the second channel according to the inputted channel sequence data, the first delivery data, and the second delivery data;

wherein the first channel is located on a first infusion pump and the second channel is located on a second infusion pump, further wherein the first infusion pump and the second infusion pump are in communication with each other.

5. The method of claim 4 wherein the first infusion pump and the second infusion pump are detachably coupled to each other.

6. The method of claim 1 wherein the delivery data includes at least one of fluid identification data, dosage data, rate data, fluid volume data, or delivery time data.

7. A method for controlling at least one infusion pump, the method comprising:

inputting channel sequence data into a processor in electronic communication with the at least one infusion pump, wherein the channel sequence data identifies a sequence for delivering a first fluid from a first channel and a second fluid from a second channel; and then inputting into the processor first delivery data for the first channel and second delivery data for the second channel;

delivering the first fluid from the first channel and second fluid from the second channel according to the inputted channel sequence data, the first delivery data, and the second delivery data; and displaying data from a group consisting of the infusion data for a selected channel when fluid is being delivered from the selected channel, the channel sequence data, first delivery data, and second delivery data.

8. The method of claim 1 further comprising a step of controlling a delivery of a keep vein open therapy after delivery of the first fluid and the second fluid.

9. The method of claim 1 wherein the at least one infusion pump comprises a first tube set operably coupled to the first channel and a second tube set operably coupled to the second channel, wherein when the first fluid is being delivered from the first channel, the second tube set is capable of being removed from the second channel.

10. A method for controlling at least one infusion pump, the method comprising:

inputting channel sequence data into a processor in electronic communication with the at least one infusion pump, wherein the channel sequence data identifies a sequence for delivering a first fluid from a first channel and a second fluid from a second channel; and then inputting into the processor first delivery data for the first channel and second delivery data for the second channel;

delivering the first fluid from the first channel and second fluid from the second channel according to the inputted channel sequence data, the first delivery data, and the second delivery data; and displaying an indication of current execution status within the sequence during the delivering step.

* * * * *